(12) United States Patent
Tsampazis et al.

(10) Patent No.: US 8,788,032 B2
(45) Date of Patent: Jul. 22, 2014

(54) METHOD AND CIRCUITRY FOR MEASUREMENT OF STIMULATION CURRENT

(75) Inventors: Kostas Tsampazis, Sidney (AU); Adrian Cryer, Sidney (AU); Andrew Saldanha, Sidney (AU)

(73) Assignee: Cochlear Limited, Macquarie University, NSW (AU)

( * ) Notice: Subject to any disclaimer, the term of this patent is extended or adjusted under 35 U.S.C. 154(b) by 29 days.

(21) Appl. No.: 12/892,766

(22) Filed: Sep. 28, 2010

(65) Prior Publication Data

US 2011/0077698 A1    Mar. 31, 2011

(30) Foreign Application Priority Data

Sep. 28, 2009 (AU) ................................ 2009222439

(51) Int. Cl.
 *A61N 1/36* (2006.01)
 *A61N 1/08* (2006.01)
(52) U.S. Cl.
 CPC ............... *A61N 1/36125* (2013.01); *A61N 1/08* (2013.01); *A61N 1/3605* (2013.01)
 USPC .................... 607/2; 607/27; 607/62; 607/137
(58) Field of Classification Search
 USPC ......................................... 607/2, 62, 27, 137
 See application file for complete search history.

(56) References Cited

U.S. PATENT DOCUMENTS

| | | | |
|---|---|---|---|
| 4,261,372 A | 4/1981 | Hansen et al. | |
| 4,419,995 A | 12/1983 | Hochmair et al. | |
| 4,532,930 A | 8/1985 | Crosby et al. | |
| 5,167,236 A | 12/1992 | Junker | |
| 5,443,493 A | 8/1995 | Byers et al. | |
| 5,645,585 A | 7/1997 | Kuzma | |
| 5,749,912 A | 5/1998 | Zhang et al. | |
| 5,795,287 A | 8/1998 | Ball et al. | |
| 5,814,095 A | 9/1998 | Muller et al. | |
| 5,833,714 A | 11/1998 | Loeb | |
| 6,070,105 A | 5/2000 | Kuzma | |
| 6,112,124 A | 8/2000 | Loeb | |
| 6,129,753 A | 10/2000 | Kuzma | |
| 6,198,971 B1 | 3/2001 | Leysieffer | |
| 6,259,951 B1 | 7/2001 | Kuzma et al. | |
| 6,442,422 B1 * | 8/2002 | Duckert ........................ 600/547 |

(Continued)

FOREIGN PATENT DOCUMENTS

| | | |
|---|---|---|
| AU | 2002244531 | 10/2002 |
| WO | WO 90/07251 | 6/1990 |

(Continued)

OTHER PUBLICATIONS

Examiner's First Report, Australian Application No. 2009222439 mailed Jul. 12, 2010 (3 pages).

(Continued)

*Primary Examiner* — Christopher D Koharski
*Assistant Examiner* — Philip Edwards
(74) *Attorney, Agent, or Firm* — K&L Gates, LLP

(57) ABSTRACT

A method and device for measuring and controlling stimulation current, for example in an implantable device, are disclosed. A series capacitor ($C_b$) is disposed along the conduction path, and the voltage ($U_c$) across the capacitor measured, so as to provide a direct measurement of the delivered stimulation current.

26 Claims, 9 Drawing Sheets

(56) References Cited

U.S. PATENT DOCUMENTS

| | | |
|---|---|---|
| 6,537,200 B2 | 3/2003 | Leysieffer et al. |
| 6,537,700 B1 | 3/2003 | Ovshinsky et al. |
| 6,549,814 B1 | 4/2003 | Strutz et al. |
| 6,565,503 B2 | 5/2003 | Leysieffer et al. |
| 6,575,894 B2 | 6/2003 | Leysieffer et al. |
| 6,671,559 B2 | 12/2003 | Goldsmith et al. |
| 6,697,674 B2 | 2/2004 | Leysieffer |
| 7,194,314 B1 | 3/2007 | Richter et al. |
| 7,315,763 B2 | 1/2008 | Kuzma et al. |
| 7,937,154 B2 | 5/2011 | Risi |
| 2003/0191510 A1* | 10/2003 | Ochs et al. ............... 607/62 |
| 2004/0172118 A1 | 9/2004 | Gibson |
| 2004/0236390 A1 | 11/2004 | Dadd et al. |
| 2005/0080473 A1 | 4/2005 | Gibson et al. |
| 2006/0079950 A1 | 4/2006 | Lehnhardt et al. |
| 2007/0055318 A1 | 3/2007 | Forsberg et al. |
| 2007/0055322 A1 | 3/2007 | Forsberg et al. |
| 2007/0135868 A1 | 6/2007 | Shi et al. |
| 2007/0135885 A1 | 6/2007 | Risi |
| 2007/0162098 A1 | 7/2007 | Risi et al. |
| 2007/0282416 A1 | 12/2007 | Gibson et al. |
| 2012/0078337 A1 | 3/2012 | Darley et al. |

FOREIGN PATENT DOCUMENTS

| | | |
|---|---|---|
| WO | WO 96/31087 | 10/1996 |
| WO | WO 97/26943 | 7/1997 |
| WO | WO 97/21324 | 12/1997 |
| WO | WO 00/69512 | 11/2000 |
| WO | WO 02/080817 | 10/2002 |
| WO | WO 2004/052444 | 6/2004 |
| WO | WO 2006/136961 | 12/2006 |
| WO | WO 2007/030635 | 3/2007 |
| WO | WO 2007/030636 | 3/2007 |
| WO | WO 2007027879 | 3/2007 |
| WO | WO 2010/011721 | 1/2010 |

OTHER PUBLICATIONS

C. Amerijckx et al., "An electronic device for nerve stimulation", Workshop on Industrial Microtechnology Applications, Oct. 15-16, 1998, Madrid (Spain) (4 pages).

E J Slater, "A meter for the measurement of pulse amplitude from electrical nerve stimulators", Clin. Phys. Physiol. Meas. 1984, vol. 5, No. 2, 111-113 (3 pages).

English Translation of Notice of Reasons for Rejection for JP 2002-578856 dated Jan. 15, 2008 (3 pages).

AU Examiner's Report for AU 2006202622 dated Apr. 14, 2008.

International Preliminary Examination Report for PCT/AU02/00433 dated Sep. 5, 2002.

English Translation of Notice of Reasons for Rejection for JP 2002-578856 dated Aug. 5, 2008.

J Ito et al., "Tinnitus Suppression by Electrical Stimulation of the Cochlear Wall and by Cochlear Implantation," Department of Otolaryngology, Otsu Red Cross Hospital, Japan, The Laryngoscope vol. 104 (6 Pt. 1), Jun. 1994, pp. 752-754.

M. Sakajiri et al., "A method for Suppressing Tinnitus by Electrical Stimulation to Cochlea and Remedial value, "Research Institute for Electric Science, Hokkaido University, Sapporo, Japan, Journal of the Acoustical Society of Japan (E), vol. 17, No. 6, pp. 453-455, Nov. 1993.

W. McKerrow et al., "Tinnitus Suppression by Cochlear Implants," Coleman and Ebstein Laboratories Department of Otolaryngology, University of California, San Francisco, The Annals of Otology, Rhinology & Laryngology, Jul. 1991, vol. 100 (7), pp. 552-558.

International Search Report for PCT/AU02/00433, dated May 28, 2002.

* cited by examiner

METHOD AND CIRCUITRY FOR MEASUREMENT OF STIMULATION CURRENT

RELATED APPLICATIONS

This application claims priority to Australian Patent Application No. 2009222439 filed Sep. 28, 2009, the entire contents of which are hereby incorporated by reference herein.

BACKGROUND

1. Field of the Invention

The present invention relates generally to implantable stimulating devices, and more particularly to the measurement and control of stimulation current in implantable stimulating devices.

2. Related Art

The delivery of electrical stimulation has become an established part of medical therapy. Electronic devices are implanted within the body in order to stimulate nerve tissue (e.g. cochlear implants) for perceptual or functional purposes. Such electronic devices commonly use platinum electrodes as the interface between the electronics and the body tissue. In general terms, such electrodes are selectively driven with a current in order to evoke a perception (for example sound) or a function (for example a limb movement) in the user. FIG. 8 provides a schematic illustration of a system for application of electrical stimulation. As illustrated, a plurality of platinum electrodes 4 are connected to an implant 2 via insulated wires 5 and driven by a stimulating current 6 from a current source 3. The stimulating current passes 7 through the tissue 1 and the nerve cell 8, and returns to the implant 2.

It is usual for the stimulating current to be structured as biphasic pulses, in such a way that there is no net charge delivered to the tissue. If, however, the stimulating current is allowed to flow in one direction for too long, toxic products can escape the interface and damage or destroy the surrounding tissue.

The use of charge-neutral pulses (i.e., pulses with a net charge of 0) ensures, in principle, that the requirement that net charge delivered to the tissue is zero is met. In practice, however there will be a small error in the generated stimulation current. Further, if the stimulation current source goes out of compliance, then significant charge errors can occur.

Existing cochlear implants do not readily permit the measurement of stimulation current during stimulation. Presently, voltage telemetry measurements are recorded for a stimulation electrode in vivo as an indication of the existence of the stimulation current. It is assumed that the stimulation current has the amplitude (value) that the current source has been set to generate.

In practice, the value of the stimulation current can be different that the value to which the current source has been set. For example, if the current source is out of compliance, (e.g. when the electrode impedance is higher than normal) then the amplitude of the stimulation current may be much lower than the value to which the current source is set. Or, if there is a current leakage at the stimulation electrode circuitry, (e.g. a fault condition) then the leakage current adds to the stimulation current, resulting in an increase of the current flow between the stimulation electrodes. This increased current flow can vary from very small to very large values depending on the degree of leakage. A user reporting a hearing sensation and/or pain at low stimulation current levels may indicate that the stimulation current is not effectively controlled by the current source.

SUMMARY

According to one aspect of the present invention, there is provided a neural stimulator, comprising: a plurality of stimulation electrodes; at least one controllable electrical stimulator configured to deliver electrical stimuli via at least one of the stimulation electrodes; a capacitor disposed in series along a conduction path including the at least one stimulation electrode and the controllable electrical stimulator; and a voltage measurement device configured to measure the voltage across the capacitor, said voltage providing an indication of the current operatively delivered by said at least one stimulation electrode.

According to another aspect, there is provided a method of monitoring stimulation current in a neural stimulator, the stimulator including an electrical stimulator, and a plurality of stimulation electrodes, the method comprising: disposing a capacitor in a conduction path of at least one of the stimulation electrodes; measuring a voltage across said capacitor during stimulation of said electrode; and determining, from said measured voltage, the stimulation current delivered to said electrode.

BRIEF DESCRIPTION OF THE DRAWINGS

Illustrative embodiments of the present invention will now be described with reference to the accompanying figures, in which.

DETAILED DESCRIPTION

Figure 1:
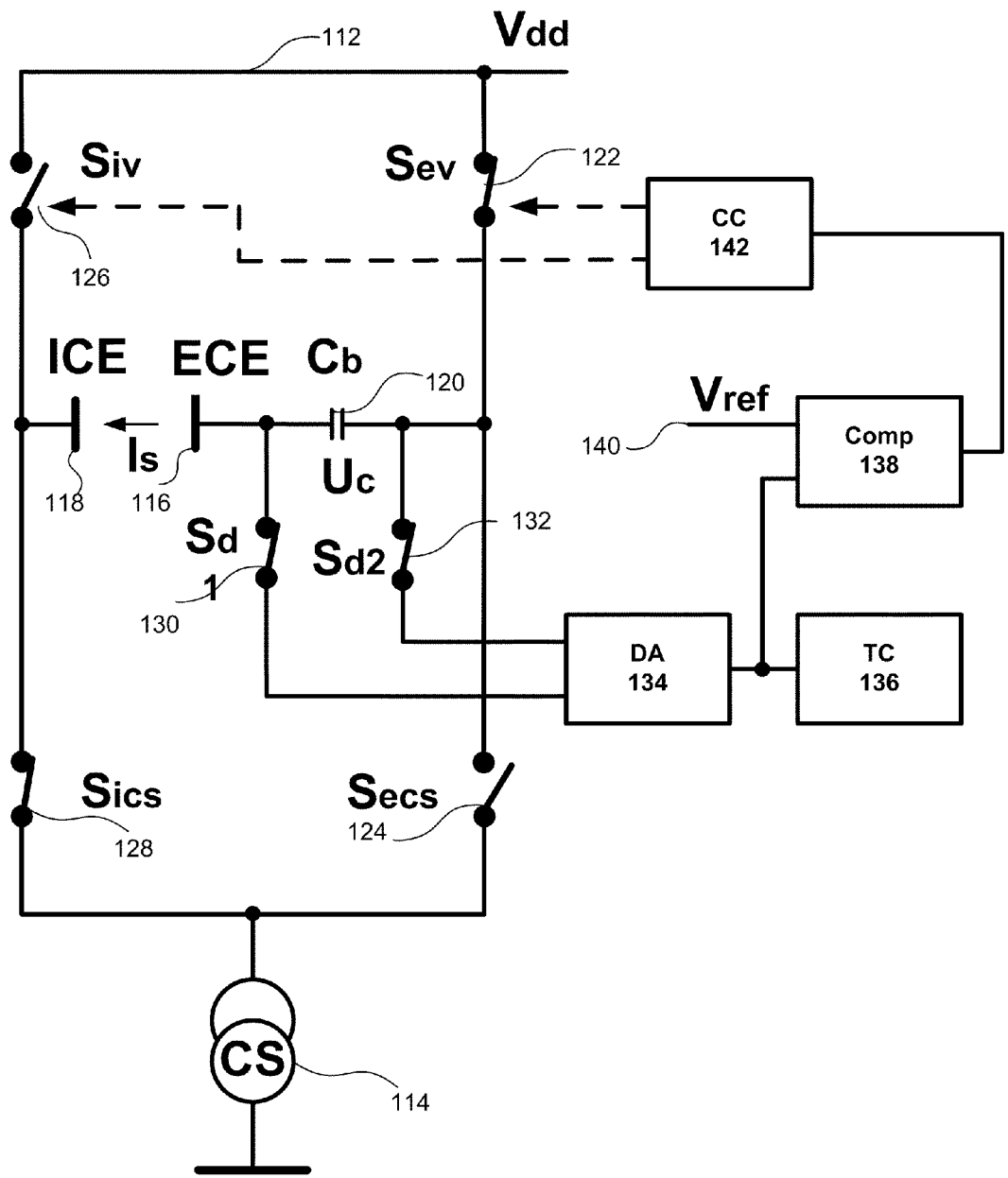
FIG. 1 is a schematic diagram of a current measurement circuit, in accordance with an embodiment of the present invention.

An aspect of the present invention provides a capacitor in series with the current source and the electrode, and measures the voltage across the capacitor in order to monitor the delivered stimulation current.

Aspects of the present invention will be described with reference to a particular illustrative example, which is a device intended for use in a cochlear implant stimulation system. However, it will be appreciated that the present invention is applicable wherever electrical stimuli are required to be delivered within the body. This may include, for example, muscle and neural stimulators, in applications including (without limitation) tremors, Parkinson's disease, chronic pain, epilepsy, visual systems, incontinence treatments, cardiac related devices, muscle stimulation systems, and the like. This further includes hearing prostheses, including intra-cochlear devices, brain stem implants, and other electrical stimulation devices. Additionally, embodiments of the present invention may be used in hearing systems in combination with acoustic or mechanical stimulation, for example in hybrid type systems; or, for example, a system with fully implanted components, or a system including external components as well as implanted components.

It will be appreciated that the presently described implementation(s) is described for illustrative purposes, and its features are not intended to be limitative of the scope of the present invention. Many variations and additions are possible within the scope of the present invention, and it would be expected that a wide variety of other aspects of such systems would also be employed in any practical system.

The examples below relate to the electrical stimulation part of a cochlear implant system. It will be appreciated that aspects of the invention can be employed with conventional systems for other aspects of a practical device, for example microphones, sound processing, sound and speech processing, mapping sound and speech to electrical stimuli, constructing electrodes, and so forth. Exemplary prostheses in which aspects of the present invention may be implemented include, but are not limited to, those systems described in U.S. Pat. Nos. 4,532,930, 6,537,200, 6,565,503, 6,575,894 and 6,697,674, the entire contents and disclosures of which are hereby incorporated by reference herein. As described therein, cochlear prostheses generally include an external, wearable control unit that determines a pattern of electrical stimulation that is provided to an implanted stimulator unit containing active circuitry in a hermetic enclosure. Electrical stimuli are delivered through electrodes to provide electrical stimulation of auditory nerve cells.

As has been discussed above, the value of the stimulation current of a current source can be significantly different from the value to which the current source has been set. As will be discussed in further detail below, embodiments of the present invention may measure the actual amplitude of the stimulation current for each electrode when stimulated, and, if the actual amplitude exceeds a threshold set for the current source for a particular electrode, interrupt the stimulation in order to prevent over stimulation.

Further, in an embodiment and as will be discussed in more detail below, the external device (speech processor) of a hearing prosthesis sends power and data to the implant of the hearing prosthesis. The implant sends back telemetry data (e.g. electrode voltage, implant's identification number) to the external device (e.g., speech processor). The telemetry data received by the external device from the implant is then used by the controller of the external device to modify the power and/or the data transmitted to the implant, and thus automatically adjust the stimulation applied to the user.

In the implementation described below, a controller of an external device (or of the internal device in a totally implanted system) uses stimulation current telemetry data to modify the data and/or the power transmitted by the external device to the implant. In other words, the telemetry signal from the implant is a feedback signal to the external device and the controller automatically responds and corrects the stimulation by modifying the data and/or the power transmitted to the implant (self adjustment, adaptive stimulation).

As discussed above, electrical stimuli for neural stimulators are generally delivered as biphasic stimuli. In phase 1, the current pulse is delivered with a first polarity, to provide the desired neural stimulation. In phase 2, a current pulse of opposite polarity is applied. This opposite polarity of phase serves to compensate for the charge delivered in phase 1, so that a net charge of 0 is delivered to the user.

The voltage u(t) over a capacitor C is proportional to the charge q(t) that has passed through the capacitor C. The accumulated charge is equal to the integral of the current i(t), thus the voltage over a capacitor C is also proportional to the current i(t).

$$u(t)=q(t)/C=(1/C)\int i(t)dt$$

In an implementation, the biphasic stimuli comprise two phases each having a constant current level and an equal duration, but having opposite polarities (e.g., a shape similar to a square wave). As the amplitude of the stimulation current is constant (Is) during each phase in this implementation, the voltage over the capacitor increases or decreases linearly during each phase.

The slope of the voltage increase or decrease, dU/dt, is proportional to both the amplitude of the stimulation current and the rate of change of the charge:

$$I=C(dU/dt)=dq/dt$$

The voltage over the capacitor, C, measured at any time during phase 1 or phase 2 is proportional to the charge delivered up to the time of measurement as well as to the amplitude of the stimulation current. The voltage over the capacitor measured when no stimulation current flows (at the end of phase 1, during the interphase gap and at the end of phase 2) is proportional to the charge delivered.

In the below discussed embodiment of FIG. 1, the illustrative method and circuitry for measurement of stimulation current in vivo is based, in broad terms, on measurement of the voltage developed on a capacitor by the stimulation current flow. As illustrated, the capacitor is connected in series with a stimulation electrode and the stimulation current flows through it. Since the stimulation current is (in principle) constant during both phases, the voltage on the capacitor increases linearly during Phase 1, remains unchanged during the interphase gap and decreases linearly to zero during Phase 2. The voltage on the capacitor is proportional to the stimulation current value and is measured with a differential amplifier connected to the capacitor. The measured voltage is applied to a telemetry circuitry and to a comparator that triggers a switch control circuit. The switch circuit interrupts the stimulation to prevent over stimulation if the stimulation current exceeds its set value. The telemetry measured current values can be used for accurate calculation of the electrode-tissue impedance and for diagnostic purposes (e.g. electrical condition of the stimulation circuitry).

The measured voltage on the capacitor is transmitted to the speech processor for further processing and diagnosing as well as for stimulation control—for example, stimulation pulse amplitude and duration control (to prevent unbalanced charge and over stimulation) or power control (to save battery life). It will be appreciated that it is known to measure the voltage across the electrodes, and provide this value as telemetry. Providing a measured current value allows for accurate calculation of values such as tissue impedance.

FIG. 1 illustrates a simplified circuit diagram of one implementation of a measuring circuit 100 that may be used for measuring current values, in accordance with an embodiment of the present invention. This exemplary circuit 100 may be implemented, for example, in a stimulator unit of a cochlear implant. As illustrated the exemplary measurement circuit of FIG. 1 comprises the following components and signals.

$V_{dd}$ 112 is a power supply rail;
CS 114 is a current source;
ECE 116 is an extracochlear electrode;
ICE 118 is an intracochlear electrode;
$C_b$ 120 is a capacitor connected in series with the extracochlear electrode ECE 116;
$S_{ev}$ 122 and $S_{ecs}$ 124 are switches associated with the ECE 116;
$S_{iv}$ 126 and $S_{ics}$ 128 are switches associated with the ICE 118;
$S_{d1}$ 130 and $S_{d2}$ 132 are switches controlling the inputs to the differential amplifier (DA) 134;
$I_s$ is the stimulation current flowing between ECE 116 and ICE 118;
$U_c$ is the voltage on the capacitor $C_b$ 120 developed by the stimulation current Is;
DA 134 is a differential amplifier;
TC 136 is a telemetry circuit;
Comp 138 is a comparator;
Vref 140 is a reference voltage for the comparator (corresponds to the stimulation current value for a particular electrode); and
CC 142 is control circuitry.

In this example, a biphasic current flows between ECE 116 and ICE 118 through the capacitor, $C_b$, 120, in applying stimulation to the spiral ganglion cells. In a monopolar mode, in this example, the biphasic current flows from the ECE 116 to the ICE 118 in phase 1 and from the ICE 118 to the ECE 116 in phase 2.

Figure 2:
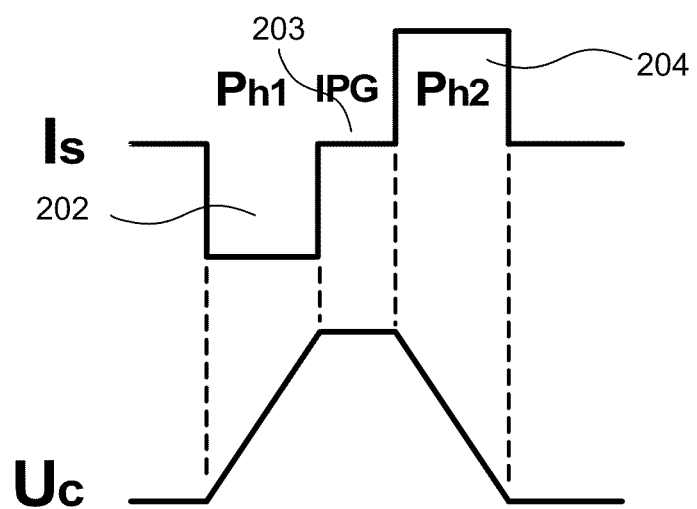
FIG. 2 is a graph of charge and current for a biphasic stimulation, in accordance with an embodiment of the present invention.

FIG. 2 illustrates an exemplary stimulation current signal, $I_s$ and the corresponding voltage, $U_c$, on the capacitor $C_b$ 120, where x-axis represents time. As illustrated, in this example, the current flowing during each phase 202 and 204 (i.e., Ph1 and Ph2) is constant. For example, as shown, each phase of the current signal, $I_s$, is a square pulse having a constant current level. Further, as shown, the current level and duration of each phase is identical, but each phase as opposite polarity. Also, as illustrated, there is an interphase gap (IPG) 203 between each phase 202 and 204.

The following provides an exemplary description of the operation of the measurement circuit 100 of FIG. 1 using the exemplary stimulation current signal, Is, of FIG. 2. During Phase 1 (Ph1) 202, stimulation current, $I_s$, flows from the power supply rail, $V_{dd}$, 112 through electrode switch, $S_{ev}$, 122 across capacitor $C_b$ 120 through extracochlear electrode ECE 116, through the tissue to ICE 118, and through switch $S_{ics}$ 128 to current source (CS) 114. As the stimulation current has a constant value, the voltage $U_c$ developed on the capacitor $C_b$ will increase linearly from 0 to a particular value. This particular value depends on the amplitude of the current signal $I_s$, the capacitance of $C_b$, and the duration of the current flow (i.e., the duration of Ph1 202).

As noted above, the amplitude of the current signal, $I_s$, during Ph1 202 is equal to the amplitude of the current signal, $I_s$, during (Ph2) 204. Further, in this example, during the interphase gap (IPG) all switches (i.e. $S_{ev}$ 122, $S_{ecs}$ 124, $S_{iv}$ 126, and $S_{ics}$ 128) are opened and no stimulation current flows between the electrodes ECE 116 and ICE 118.

During phase 2 204, the stimulation current flows from power supply rail $V_{dd}$ 112 through the electrode switch Siv 126, the intracochlea electrode ICE 118, the tissue between the two electrodes, the ECE 116, capacitor $C_b$ 120 and switch $S_{ecs}$ 124 to the current source 114.

The voltage, $U_c$, on the capacitor $C_b$ 120 is proportional to the value of the stimulation current. This voltage is measured by differential amplifier (DA) 134, amplified, and passed to telemetry circuit (TC) 136 and comparator (Comp) 138 for further processing.

In the illustrated example, TC 136 provides a telemetry measurement of the stimulation current for diagnostic purposes and for accurate calculation of the electrode-tissue impedance. The measured stimulation current value is informative for the condition of the electrode switching circuitry (e.g., switches 122-128, as well as switches for other intracochlea electrodes included in the cochlear implant) and the condition of the current source 114.

It will be appreciated that this example assumes a cochlear implant with an external speech processor, where telemetry data is used to control/adjust the operation of the circuit. In a totally implanted device, for example, the DA 134 output may be simply processed as an input by the implanted processor.

Comparator 138 compares the $U_c$ voltage, measured by DA 134, with a reference voltage $V_{ref}$. In this example, $V_{ref}$ is proportional to the current amplitude $I_s$ to which current source 114 is set. If the measured $U_c$ voltage is greater than the $V_{ref}$ (i.e., the measured current is greater than the set current value), then the comparator triggers the control circuitry (CC) 142. According to this implementation, the CC then interrupts the stimulation (opens the switches 122-128 associated with the stimulation electrodes ECE 118 and 116) for the remaining time of the phase duration.

During the interphase gap (IPG) all switches are opened. During the next phase (e.g., Phase 2) the current flows in the opposite direction and if the amplitude is still higher than the set value, CC 142 will interrupt the stimulation before the end of the phase duration (e.g., Phase 2). Otherwise the current will flow up to the end of Phase 2. In both cases in the presently described implementation (i.e., interrupted or not interrupted), the stimulation current, $I_s$, during the second phase, will be a charge balanced with the stimulation current, $I_s$, delivered during the first phase. Moreover, as this is responsive to the actual current and to set values (as set for the expected current source values), the interruption is not dependant on any prior assumptions or values.

Figure 3:
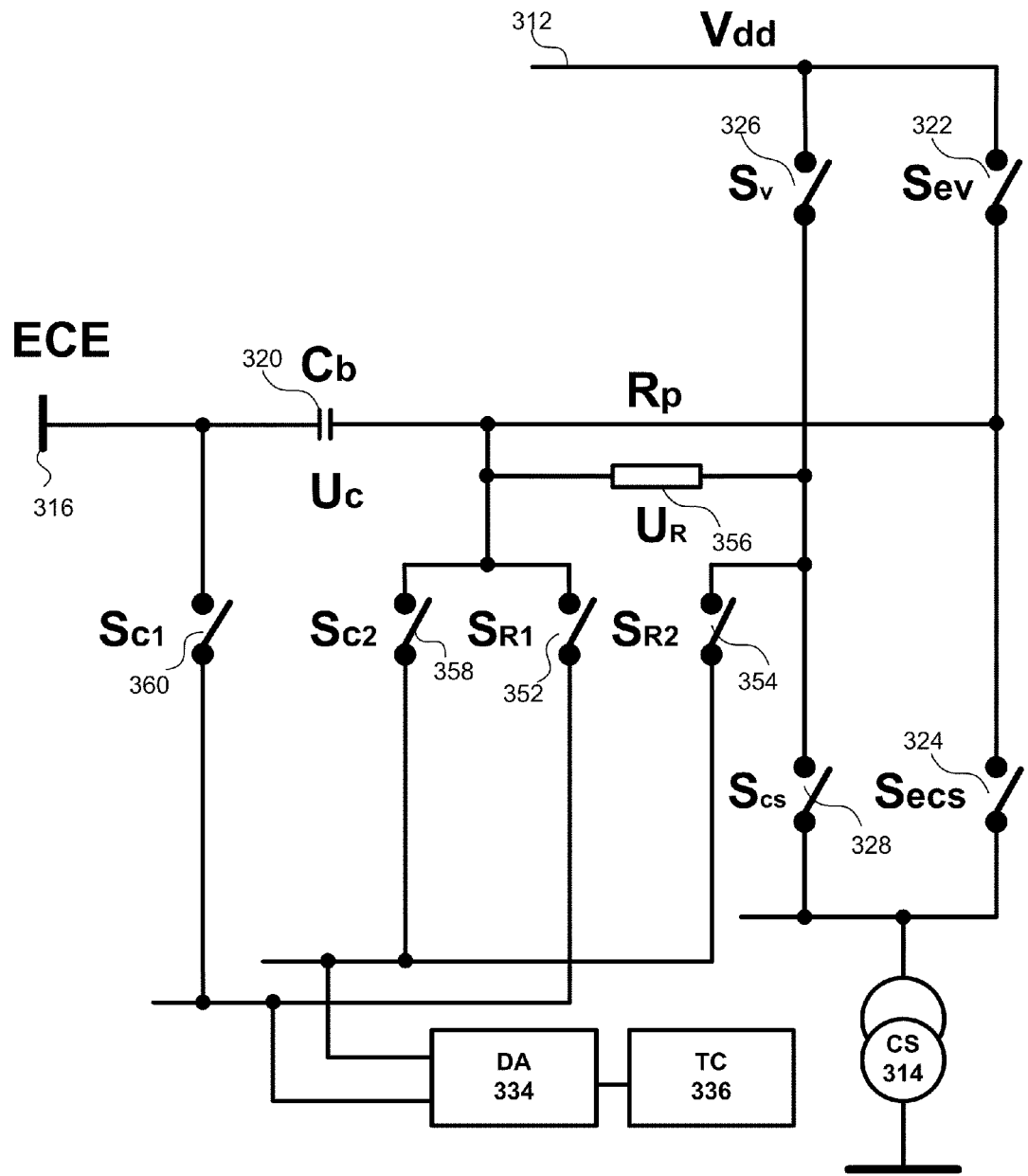
FIG. 3 is a schematic diagram of another circuit in accordance with an embodiment of the present invention.

FIG. 3 illustrates exemplary circuitry that may be used for calibrating the voltage measured over the capacitor, $C_b$. Particularly, in the implementation of FIG. 1, the voltage across capacitor $C_b$ depends on the capacitance value of the capacitor. In actual implementation, there is inherently some variation in the actual value of a capacitor, relative to the notional (i.e., specified) value of the capacitor. This actual value is typically within the specified tolerance of the capacitor. Thus, the current measurement may be subject to an error consequent from the capacitor's tolerance.

In the implementation of FIG. 3, a set of switches ($S_v$ 326, $S_{cs}$ 328) not connected to the stimulation electrodes (ECE 316, ICE (not shown)) and a precise resistor $R_p$ 356 can be used, as can be seen in FIG. 3, to calibrate the capacitance of $C_b$ 320.

In the below description of FIG. 3, the circuit 300 will described as using a stimulation current such as stimulation current, $I_s$, illustrated in FIG. 2. It should, however, be understood that in other implementations other stimulation current shapes may be used.

In the illustrated circuit, during Phase 1 202, the current flows from power supply rail $V_{dd}$ 312 through switch $S_v$ 326 precise resistor $R_p$ 356, capacitor $C_b$ 320, extracochlear electrode ECE 316, tissue, ICE (not shown) to current source CS 314. For example, although not illustrated, ECE 316 may transfer current via the tissue to an ICE (not shown). This ICE may be similar to the ICE 118 of FIG. 1 and be connected to switches similar to $S_{ics}$ 128 and $S_{iv}$ 126 of FIG. 1 that may operate in a similar manner to the switches discussed above with reference to FIG. 1.

During Phase 2 the current flows from power supply rail $V_{dd}$ 312 through the intracochlear electrode ICE (not shown), tissue, ECE 316, capacitor $C_b$ 320, precise resistor $R_p$ 356, and switch $S_{1CS}$ 328 to the current source CS 314.

As illustrated, differential amplifier DA 324 is connected to resistor $R_p$ 356 through switches $S_{R1}$ 352 $S_{R2}$ 354 and measures the voltage drop across the resistor $R_p$ 356. DA 324 feeds the measured voltage drop to telemetry circuitry TC 336. The actual value of the current amplitude for the current generated by current source CS 314 can be calculated using the telemetry measured voltage drop across the resistor and the precise resistance value of the resistor $R_p$ 356. This calculated actual current value can then be used to calibrate the voltage measured across $C_b$ 320. The voltage produced across capacitor $C_b$ by the current flow is applied to the differential voltage measurement circuitry DC through the switches SC1, SC2.

Voltage $U_c$ in relation to the current value is the base for precise calculation of the stimulation current flow between the stimulation electrodes. The circuit shown in FIG. 3 allows the current generated by the Current Source 114 to be measured precisely and the measured value to be used for calibration purposes ($U_c$ voltage on the capacitor $C_b$). After calibration, the switches of FIG. 3 may be appropriately opened and closed so that current does not pass through resistor $R_p$ 356 during application of stimulation to the user.

Figure 6:
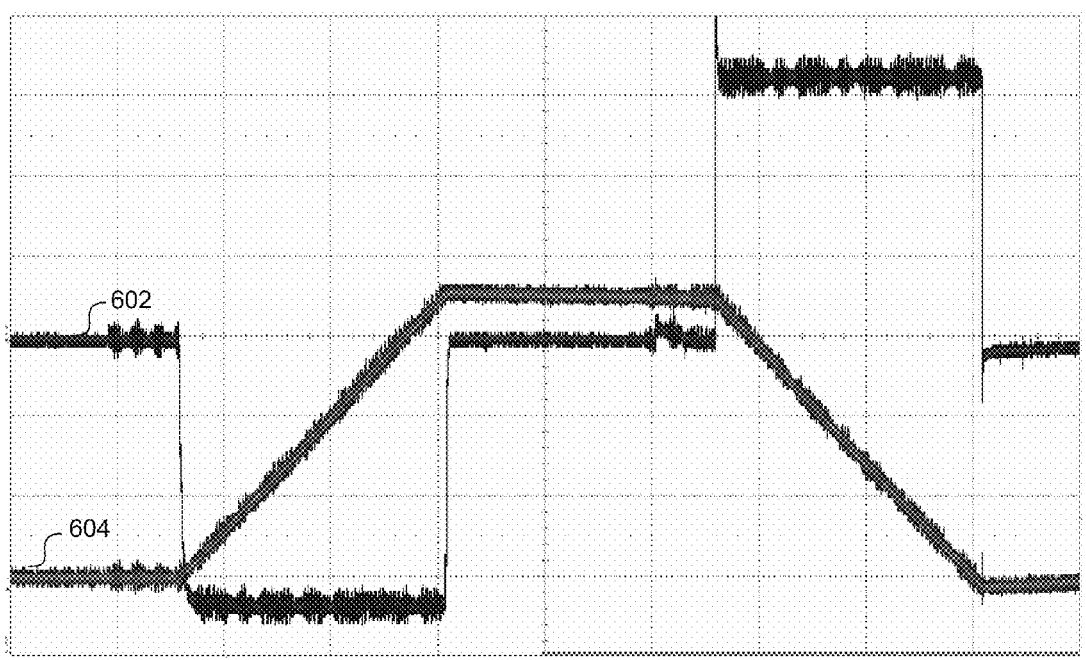
FIG. 6 is a screen shot illustrating an oscillogram of the voltage over a resistor and a capacitor during operation, in accordance with an embodiment of the present invention.

FIG. 6 illustrates an exemplary oscilloscope trace of the voltage 602 across the resistor Rp 356 and the voltage 604 across the capacitor Cb 320 of FIG. 3. As illustrated, the steady voltage across the resistor, $R_p$ 356, and the gradual build up and reduction of voltage across the capacitor, $C_b$ 320 can be seen.

Figure 7A:
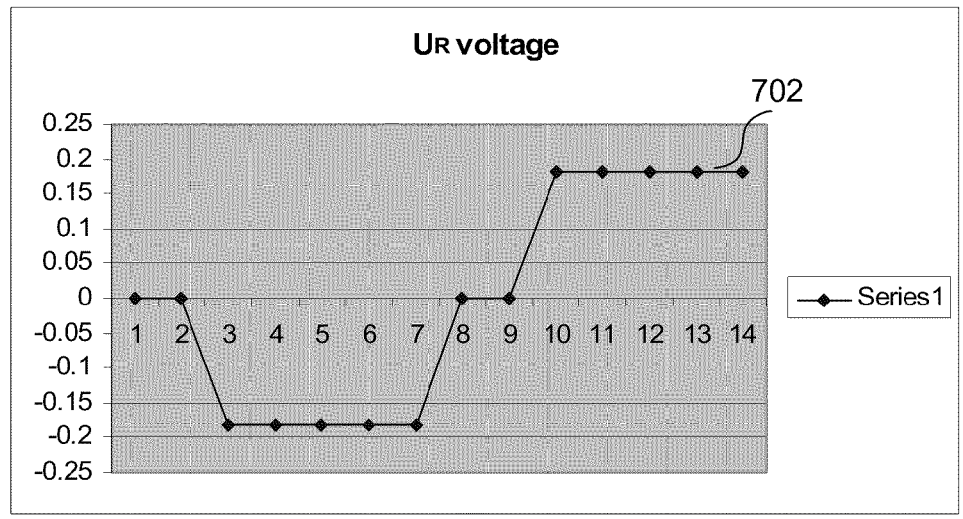
FIG. 7a is a graph illustrating the telemetry measured voltage across the series resistor, in accordance with an embodiment of the present invention.
Figure 7B:
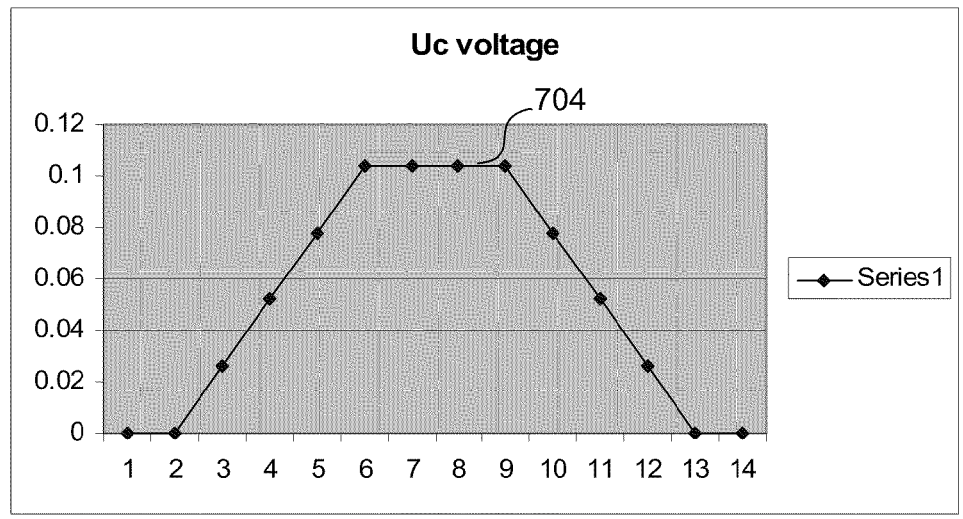
FIG. 7b is a graph illustrating the telemetry measured voltage across the capacitor according to the same implementation as FIG. 7a, in accordance with an embodiment of the present invention.
Figure 8:
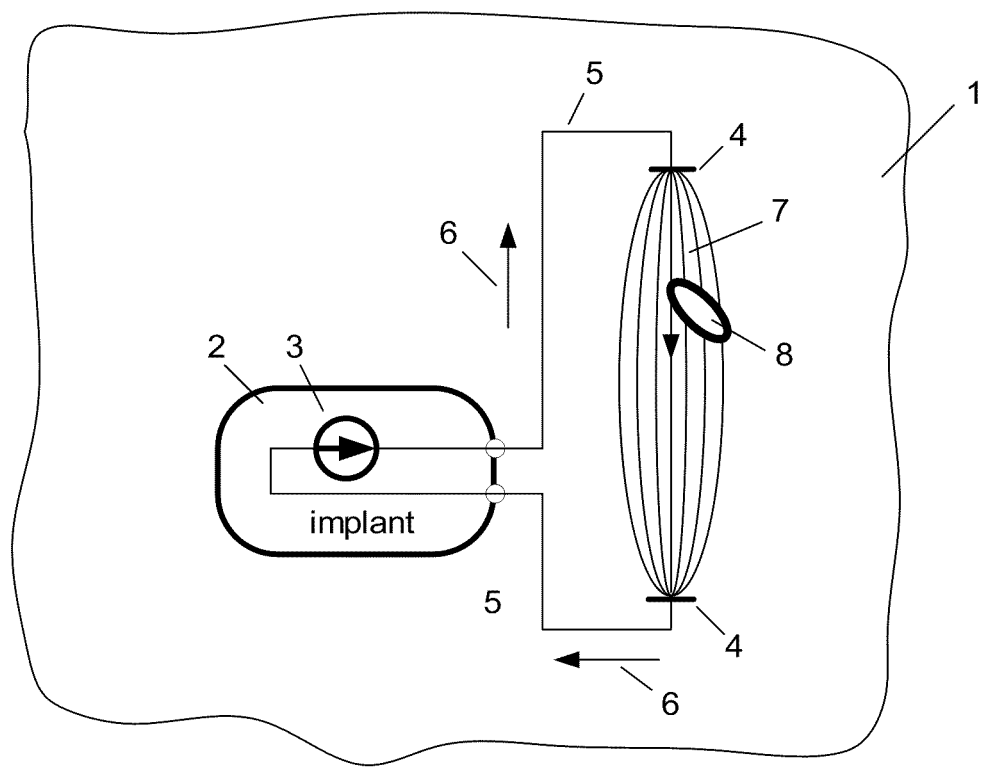
FIG. 8 is a schematic illustration of electrical stimulation, in accordance with an embodiment of the present invention.

FIGS. 7a and 7b provide exemplary graphs of telemetry values for the voltage 702 across the resistor, $R_p$, 356 and the voltage 704 across the capacitor, Cb, 320 of FIG. 3, where the illustrated data points (i.e., the dots) are the measured values and the line is the interpolated values between these measured values. It is noted that in a practical implementation, the calibration process may be adequately performed only periodically, for example at start up. Further, so that a single comparator may be used, the resistor and capacitor measurements may be undertaken at different times on the same circuit.

Figure 4:
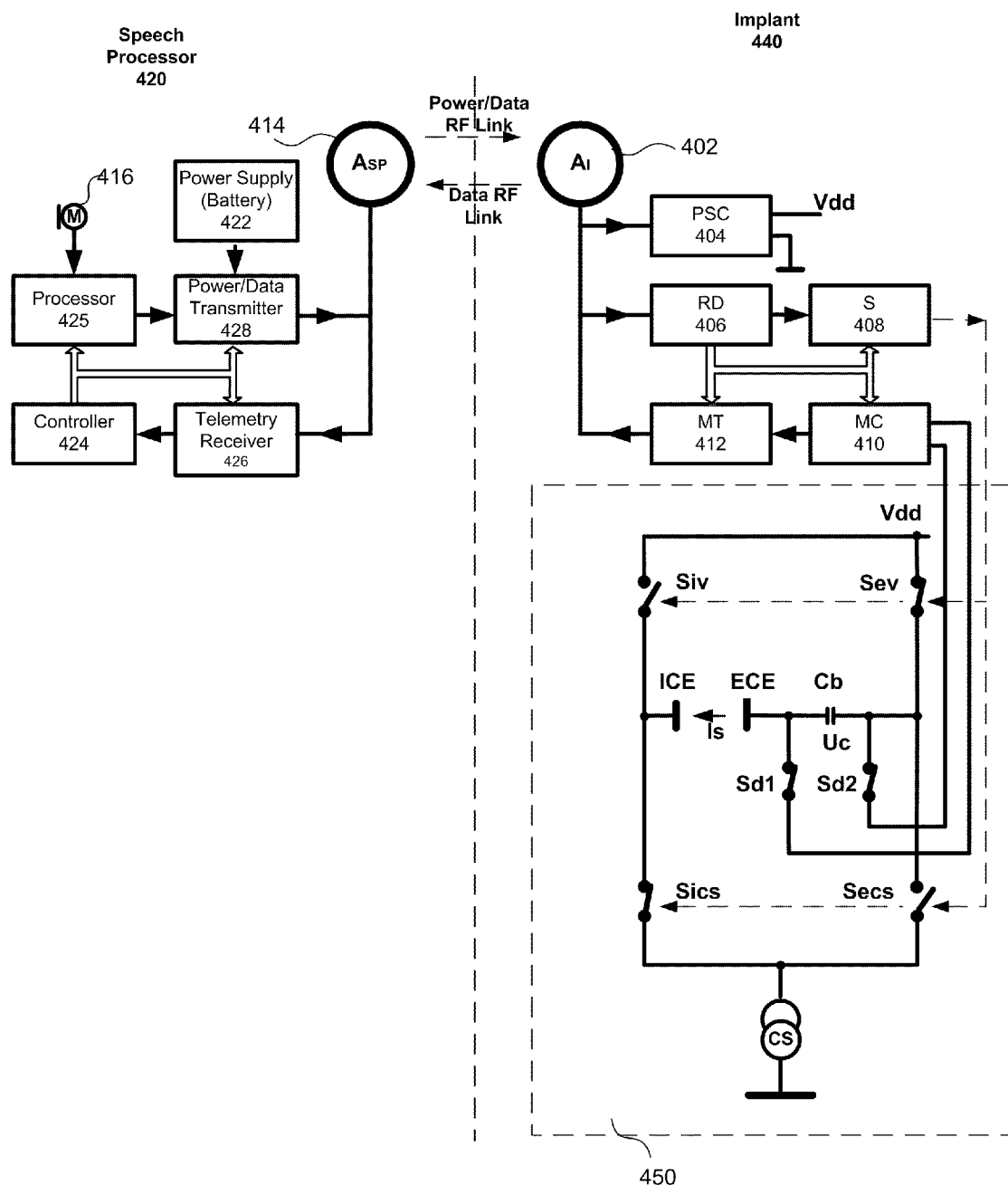
FIG. 4 provides a simplified block diagram of an Implant/Speech Processor system comprising a measurement circuit, in accordance with an embodiment of the present invention.

FIG. 4 provides a simplified block diagram of an Implant/Speech Processor system comprising a measurement circuit, such as discussed above. In FIG. 4, AI 402 is the implant's antenna;
PSC 404 is a power supply circuit;
R/D 406 is a receiver-demodulator circuit;
S 408 is a stimulator circuit;
MC 410 is a measurement circuit;
M/T 412 is a modulator-transmitter circuit;
ASP 414 is the speech processor's antenna; and
M 416 is a microphone.

Other components are labelled as in FIG. 1. On the left side of the figure is a speech processor 420, which in this example is an external unit and includes a microphone 416 and power supply 422. The microphone output is processed by a sound processor 425, so as to provide a set of stimulation data for the implant.

The processor 425 is operable under the control of a controller 424, and is also responsive to data from the implant received by the telemetry receiver 426. In this example, power and data are transmitted together via a power/data transmitter 428 from the speech processor coil $A_{SP}$ 414 to the implanted coil $A_I$ 402

On the right side of FIG. 4 is an implant 440 that inductively receives RF signal. This RF signal may be used for a variety of purposes. For example, in this exemplary implementation, the power/data transmitter 428 of the speech processor 420 combines the data and power to be transmitted to the implant by modulating the power signal with the data. This signal is then received by the implant and processed by the PSC 404 to obtain a power supply ($V_{dd}$) for use in applying stimulation. Additionally, the R/D block 406 demodulates the received signal to retrieve the data. This data may include instructions for the implant, including stimulation instructions, which are passed to the stimulator circuitry block S 408. Modulator and transmitter M/T 412 block is used to transmit data, for example telemetry, back to the speech processor unit 420 via antennas 402 and 414.

As illustrated, 440 includes (illustrated in the bottom section of implant 440) a circuit 450 similar to measuring circuit 100 of FIG. 1. It will be appreciated that the implant stimulates an electrode array, and that, in the presently described embodiment, a circuit comparable circuit 440 is included for each electrode. In operation in using a biphasic stimulation signal (e.g., the signal, $I_s$, of FIG. 2), the voltage $U_c$ across capacitor $C_b$ at the end of Phase 1 and during the interphase gap is proportional to the stimulation current.

Figure 5:
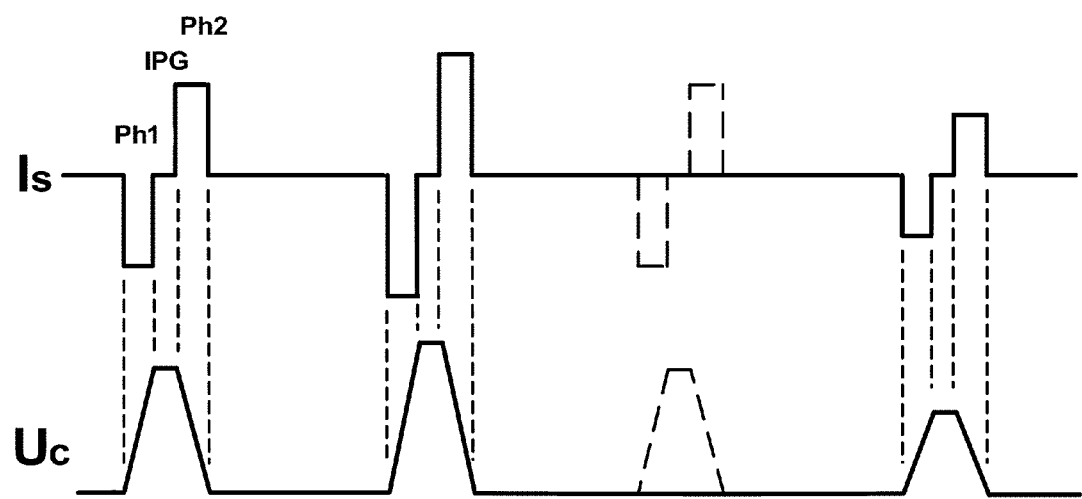
FIG. 5 is a graph showing charge and current for various stimuli against time, in accordance with an embodiment of the present invention.

FIG. 5 illustrates stimulation current $I_s$ and voltage $U_c$ against time, for successive stimulations by the Implant/Speech Processor system of FIG. 4. The values of $U_c$ track the timing of the stimulation frequency. In FIG. 5, the third current stimulation pulse ($I_c$) is missing (dotted pulse). Thus the voltage across the capacitor ($U_c$) is and remains zero. It can also be seen that although the amplitude of the current pulses varies, the capacitor is still effective to register the net charge remaining after each stimulus. The voltage, Uc, is measured by the MC block 410, and the value passed to the M/T block 412 for transmission to the speech processor 420 for further processing and control.

In the implementation of FIG. 4, the speech processor 420 employs the stimulation current telemetry data, obtained from the measurement (the voltage/charge over the capacitor) as feedback data, in order to control the stimulation by modifying the power/data transmitted to the implant and thereby optimize stimulation (for example no missing pulses) and prevent over-stimulation and/or unbalanced charge stimulation.

The measured stimulation current value can be used for diagnostic purposes, so that the measured stimulation current value is compared with the set current value for each electrode. Any missing stimulation pulses or pulses with inappropriate amplitude can be detected. The measured values can be used, for example, to determine that a serious fault condition applies to one electrode and that it should be removed from the electrode map.

The measured voltage, $U_c$, value can also be used for safety purposes. The voltage across the capacitor ($U_c$) at the end of phase 2 is proportional to phase 1-phase 2 charge difference. Any variation in phase 1 or phase 2 pulse amplitude and/or pulse duration results in unbalanced charge stimulation, and hence leaves a net charge across $C_b$. The $U_c$ voltage measured is informative for the stimulation condition (charge balance) and can be used as feedback to interrupt the stimulation in order to prevent unbalanced charge stimulation. In the case that the measured stimulation current value exceeds its set value for a particular electrode the stimulation can automatically be interrupted in order to prevent over stimulation.

Figure 9:
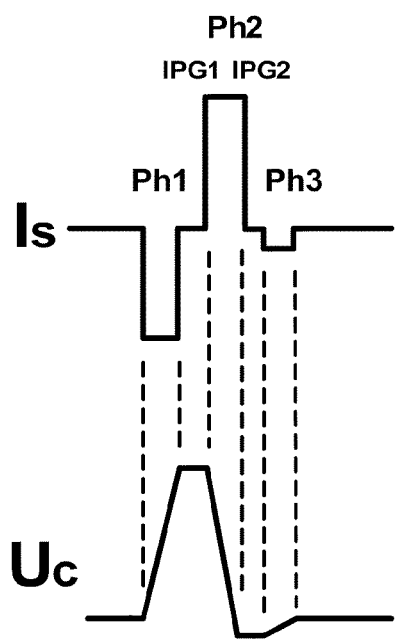
FIG. 9 is a graph of charge and current against time for triphasic stimulus, in accordance with an embodiment of the present invention.
Figure 10:
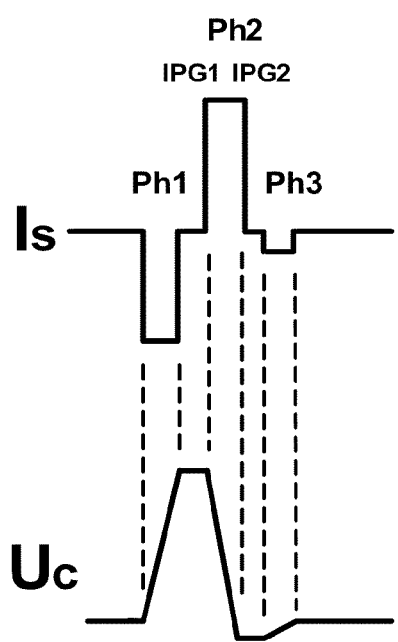
FIG. 10 is a graph of charge and current against time for another triphasic stimulus, in accordance with an embodiment of the present invention.

It will be appreciated that the present invention is not limited in scope to any particular form of electrical stimulus. Whilst it is discussed in the context of a biphasic pulse, any type of electrical stimulus, having different polarity components, can be monitored and controlled using the present invention. FIGS. 9 and 10 illustrate triphasic pulses, having two pulses in one polarity and one in the other, but still overall delivering no net charge (in principle) to the user.

Similarly, whilst the invention is applicable to current sources, it will be understood that the current source could for example, take different values for parts of a single phase of stimulation. Whilst the present invention has been discussed in the context of a single current source, it is applicable in the context of any suitable arrangement, for example the use of a current source and current sink associated with each electrode, a switched matrix approach to providing current, or any other suitable arrangement. Whilst the illustrative implementation is to monitor a capacitor in series with the extra-cochlear electrode, so as to monitor stimulation current for all monopolar stimulation, embodiments of the invention could be deployed using a capacitor monitored in series with each intra-cochlear electrode, so as to be applicable to bipolar stimulation as well, current steering techniques, and the like. In such an arrangement, a single high accuracy resistor could be used, with suitable switching, to calibrate all the series capacitors.

What is claimed is:

1. A neural stimulator, comprising:
a plurality of stimulation electrodes;
at least one controllable electrical stimulator, including a current source, configured to deliver electrical stimuli via at least one of the stimulation electrodes;
a capacitor disposed in series along a conduction path including the at least one stimulation electrode and the controllable electrical stimulator such that the conduction path, during delivery of the electrical stimuli, further includes the current source disposed in series with the capacitor; and
a voltage measurement device configured to measure the voltage across the capacitor, said voltage providing an indication of the current operatively delivered by said at least one stimulation electrode.

2. A neural stimulator according to claim 1, wherein the value of the voltage across the capacitor after each stimulus provides an indication of the charge operatively delivered by said at least one stimulation electrode.

3. A neural stimulator according to claim 1, wherein the neural stimulator is configured to modify, in response to said measured voltage, one or more parameters of said electrical stimulator so as to modify the stimulus delivered.

4. A neural stimulator according to claim 1, further comprising:
a comparator configured to compare said measured voltage against a reference value and output a result thereof; and
a control circuit configured to selectively interrupt delivery of said stimuli according to the comparison result.

5. A neural stimulator according to claim 1, wherein:
the neural stimulator is configured as an operative component adapted for a hearing prosthesis.

6. A neural stimulator according to claim 5, wherein:
the stimulation electrodes are configured for insertion into at least one of a cochlea and tissue proximal thereto.

7. A neural stimulator according to claim 6, wherein:
at least one of the cochlear electrodes is configured for intracochlear placement; and
at least one of the cochlear electrodes is configured for extracochlear placement.

8. A neural stimulator according to claim 1, wherein:
along the conduction path, a segment thereof includes the capacitor disposed in series with the at least one stimulation electrode;
the neural stimulator further comprises:
a first switch disposed between a first end of the segment and the electrical stimulator;
a second switch disposed between a second end of the segment and the electrical stimulator; and
a control circuit configured at least to selectively:
open the second switch and close the first switch during a first phase so as to achieve a first arrangement of the conduction path according to which current flows through the segment in a first direction; and
open the first switch and close the second switch during a second phase so as to achieve a second arrangement of the conduction path according to which current flows through the segment in a second direction.

9. A neural stimulator according to claim 1, wherein:
the voltage measurement device includes a differential amplifier that has non-inverting and inverting inputs; and
first and second ends of the capacitor are connected to the non-inverting and inverting inputs, respectively, of the differential amplifier.

10. A neural stimulator according to claim 1, wherein:
an electrical connection between the capacitor and the at least one stimulation electrode of the conduction path is:
at least an indirect type of electrical connection; and
an unswitched type of electrical connection.

11. A neural stimulator according to claim 1, wherein:
the at least one controllable electrical stimulator is a first controllable electrical stimulator;
the capacitor is a first capacitor;
the voltage measurement device is a first voltage measurement device;
the arrangement of the first controllable electrical stimulator, the first capacitor and the first voltage measurement device defining a first set of components;
there are N stimulation electrodes in the plurality thereof, where N is a positive integer and 2≤N;
the neural stimulator further comprises:
N controllable electrical stimulators, the at least one first controllable electrical stimulator being included therein;
N capacitors, the at least one controllable electrical stimulator being included therein; and
N voltage measurement devices, the at least one first voltage measurement device being included therein; and
for each of the N stimulation electrodes, associated therewith are N sets of components, the first set being included therein, such that, for a given one of the N stimulation electrodes, a given associated one of the N sets includes:
a corresponding one of the N of controllable electrical stimulators;
a corresponding one of the N capacitors; and
a corresponding one of the N voltage measurement devices, respectively;

the given set being arranged in a manner corresponding to the arrangement of the first set, respectively.

12. A method of monitoring stimulation current in a neural stimulator, the stimulator including an electrical stimulator, and a plurality of stimulation electrodes, the electrical stimulator including a current source, the method comprising:
disposing a capacitor in a conduction path of at least one of the stimulation electrodes;
selectively disposing, during delivery of stimulation via said electrode, the current source in the conduction path in series with the capacitor;
measuring a voltage across said capacitor during delivery of the stimulation via said electrode; and
determining, from said measured voltage, the stimulation current delivered to said electrode.

13. A method according to claim 12, further comprising:
interrupting the stimulation to said electrodes if the determined stimulation current exceeds predetermined parameters.

14. A method according to claim 12, further comprising:
selectively modifying, responsive to the determined stimulation current, one or more parameters of the electrical stimulator so as to adjust the stimulation current.

15. A method according to claim 12, wherein:
the neural stimulator is configured as an operative component adapted for a hearing prosthesis.

16. A method according to claim 15, wherein:
the stimulation electrodes are configured for insertion into at least one of a cochlea and tissue proximal thereto; and
the stimulation current to be monitored is cochlear stimulation current.

17. A method according to claim 12, wherein:
along the conduction path, a segment thereof includes the capacitor disposed in series with the at least one stimulation electrode;
the conduction path further includes:
the electrical stimulator in series with the segment;
a first switch disposed between a first end of the segment and the electrical stimulator;
a second switch disposed between a second end of the segment and the electrical stimulator; and
the disposing a capacitor in the conduction path includes:
selectively controlling the switches to:
open the second switch and close the first switch during a first phase so as to achieve a first arrangement of the conduction path according to which current flows through the segment in a first direction; and
open the first switch and close the second switch during a second phase so as to achieve a second arrangement of the conduction path according to which current flows through the segment in a second direction.

18. A method according to claim 12, wherein:
an electrical connection between the capacitor and the at least one stimulation electrode of the conduction path is:
at least an indirect type of electrical connection; and
an unswitched type of electrical connection.

19. A method according to claim 12, wherein:
the at least one electrical stimulator is a first electrical stimulator;
the capacitor is a first capacitor;
the voltage measurement device is a first voltage measurement device;
there are N stimulation electrodes in the plurality thereof, where N is a positive integer and 2≤N;
the neural stimulator further comprises:
N controllable electrical stimulators, the at least one first controllable electrical stimulator being included therein;
N capacitors, the at least one controllable electrical stimulator being included therein; and
N voltage measurement devices, the at least one first voltage measurement device being included therein;
for each of the N stimulation electrodes, associated therewith are N sets of components, the first set being included therein, such that, for a given one of the N stimulation electrodes, a given associated one of the N sets includes:
a corresponding one of the N of controllable electrical stimulators;
a corresponding one of the N capacitors; and
a corresponding one of the N voltage measurement devices, respectively;
the given set being arranged in a manner corresponding to the arrangement of the first set, respectively;
the disposing, measuring and determining are performed for at least two of the N sets of components.

20. A cochlear implant system, comprising:
a plurality of electrodes configured for insertion into at least one of a cochlea and tissue proximal thereto;
a controllable stimulator circuit, including a current source, configured to selectively deliver electrical stimuli via the electrodes;
a capacitor disposed in series along a conduction path including at least one of the electrodes and the stimulator circuit such that the conduction path, during delivery of the electrical stimuli, further includes the current source disposed in series with the capacitor; and
a voltage measurement device configured to measure the voltage across the capacitor, said voltage providing an indication of the current operatively delivered by said at least one electrode.

21. A system according to claim 20, wherein the value of the voltage across the capacitor after each stimulus provides an indication of the charge operatively delivered by said at least one electrode.

22. A system according to claim 20, further comprising:
a comparator configured to compare said measured voltage against a reference value and output a result thereof; and
a control circuit configured to selectively interrupt delivery of said stimuli by said stimulator circuit according to the comparison result.

23. A system according to claim 20, wherein:
along the conduction path, a segment thereof includes the capacitor disposed in series with the at least one stimulation electrode;
the system further comprises:
a first switch disposed between a first end of the segment and the stimulator circuit;
a second switch disposed between a second end of the segment and the stimulator circuit; and
a control circuit configured at least to selectively:
open the second switch and close the first switch during a first phase so as to achieve a first arrangement of the conduction path according to which current flows through the segment in a first direction; and
open the first switch and close the second switch during a second phase so as to achieve a second arrangement of the conduction path according to which current flows through the segment in a second direction.

24. A system according to claim 20, wherein:
the voltage measurement device includes a differential amplifier that has non-inverting and inverting inputs; and
first and second ends of the capacitor are connected to the non-inverting and inverting inputs, respectively, of the differential amplifier.

25. A system according to claim 20, wherein:
an electrical connection between the capacitor and the at least one stimulation electrode of the conduction path is:
at least an indirect type of electrical connection; and
an unswitched type of electrical connection.

26. A system according to claim 20, wherein:
the at least one controllable electrical stimulator is a first controllable electrical stimulator;
the capacitor is a first capacitor;
the voltage measurement device is a first voltage measurement device;
there are N stimulation electrodes in the plurality thereof, where N is a positive integer and 2≤N;
the system further comprises:

N controllable electrical stimulators, the at least one first controllable electrical stimulator being included therein;
N capacitors, the at least one controllable electrical stimulator being included therein; and
N voltage measurement devices, the at least one first voltage measurement device being included therein; and
for each of the N stimulation electrodes, associated therewith are N sets of components, the first set being included therein, such that, for a given one of the N stimulation electrodes, a given associated one of the N sets includes:
a corresponding one of the N of controllable electrical stimulators;
a corresponding one of the N capacitors; and
a corresponding one of the N voltage measurement devices, respectively;
the given set being arranged in a manner corresponding to the arrangement of the first set, respectively.

* * * * *